United States Patent [19]

Garcia et al.

[11] Patent Number: 5,284,838

[45] Date of Patent: Feb. 8, 1994

[54] USE OF 2,2-DIMETHYLCHROMAN-3-OL DERIVATIVES IN THE TREATMENT OF ASTHMA

[75] Inventors: Georges Garcia, Saint-Gely-du-Fesc; Richard Roux, Vailhauques; Dino Nisato, Saint-Georges d'Orques; Patrick Gautier, Cournonterral, all of France

[73] Assignee: Elf Sanofi, Paris, France

[21] Appl. No.: 19,314

[22] Filed: Feb. 18, 1993

Related U.S. Application Data

[60] Division of Ser. No. 708,194, May 31, 1991, abandoned, which is a continuation of Ser. No. 208,102, Jun. 17, 1988, abandoned.

[30] Foreign Application Priority Data

Jun. 23, 1987 [FR] France .................. 87 08830
Jan. 12, 1988 [FR] France .................. 88 00278
Mar. 9, 1988 [FR] France .................. 88 03064

[51] Int. Cl.$^5$ ............................. A61K 31/44
[52] U.S. Cl. .......................... 514/89; 514/85; 514/253; 514/254; 514/337; 544/232; 544/238; 544/337; 546/22; 546/269
[58] Field of Search .................. 514/337, 89

[56] References Cited

U.S. PATENT DOCUMENTS

| | | | |
|---|---|---|---|
| 3,707,474 | 12/1972 | Razdan et al. | 546/269 |
| 3,853,899 | 12/1974 | Fake | 546/269 |
| 3,947,462 | 3/1976 | Arendsen | 546/269 |
| 4,446,113 | 5/1984 | Evans et al. | 422/267 |
| 4,496,565 | 1/1985 | Evans et al. | 514/337 |
| 4,510,152 | 4/1985 | Faruk | 546/269 |
| 4,631,282 | 12/1986 | Cassidy | 514/254 |
| 4,782,083 | 11/1988 | Cassidy et al. | 514/337 |
| 4,971,982 | 11/1990 | Attwood | 546/269 |
| 4,999,371 | 3/1991 | Englert et al. | 514/337 |
| 5,013,853 | 5/1991 | Gericke et al. | 546/269 |
| 5,028,711 | 7/1991 | Stenzel et al. | 546/15 |
| 5,043,344 | 8/1991 | Enalert et al. | 546/269 |
| 5,043,352 | 8/1991 | Soubrie et al. | 514/456 |
| 5,071,871 | 12/1991 | Bcarea et al. | 514/337 |
| 5,071,991 | 12/1991 | Garcia et al. | 546/269 |
| 5,082,858 | 1/1992 | Garcia et al. | 514/456 |
| 5,112,839 | 5/1992 | Gericke et al. | 546/269 |
| 5,116,849 | 5/1992 | Garcia et al. | 546/269 |
| 5,130,322 | 7/1992 | Gericke et al. | 546/269 |
| 5,143,924 | 9/1992 | Gericke et al. | 546/269 |
| 5,143,936 | 9/1992 | Yamanaka et al. | 514/337 |

FOREIGN PATENT DOCUMENTS

| | | | |
|---|---|---|---|
| 87-82689 | 6/1988 | Australia . | |
| 0312432 | 4/1984 | European Pat. Off. | 546/269 |
| 0273262 | 7/1988 | European Pat. Off. | 546/267 |
| 296975 | 12/1988 | European Pat. Off. . | |

OTHER PUBLICATIONS

Chem. Abstr. vol. 109, Entry 230861 abstracting De 3,276,261 (1988).

Primary Examiner—Donald G. Duas
Attorney, Agent, or Firm—Bacon & Thomas

[57] ABSTRACT

The invention relates to 2,2-dimethylchroman-3-ol derivatives of the formula:

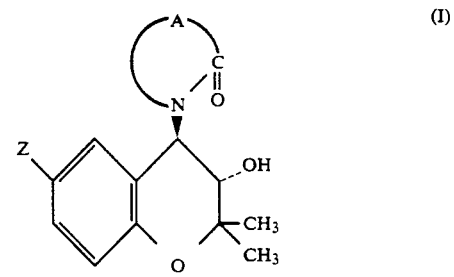

(I)

in which:

A, between N and CO, represents the group —CH=CH—E=CH— or the group

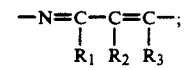

Z represents a halogen or a cyano, acetyl, trifluoroacetyl, nitro, alkylthio, carboxyl, phosphono, dialkoxy- (Abstract continued on next page.)

phosphoryl or alkoxycarbonyl group, the alkylthio and alkoxy groups containing from 1 to 3 carbon atoms;

E represents a nitrogen atom or a group $C(R_4)$;

$R_1$ represents hydrogen, a methyl group or a hydroxyl group and $R_2$ and $R_3$ each independently represent hydrogen or a methyl group, it being possible for only one of the substituents $R_1$, $R_2$ and $R_3$ to be methyl; and $R_4$ represents a hydrogen atom, a halogen atom, a methyl group or a hydroxyl group;

and to the pharmaceutically acceptable salts of the phosphono or carboxyl group.

These derivatives have an antiarrhythmic, antiasthma and antihypertensive activity.

2 Claims, No Drawings

USE OF 2,2-DIMETHYLCHROMAN-3-OL DERIVATIVES IN THE TREATMENT OF ASTHMA

This application is a division of application Ser. No. 07/708,194, filed May 31, 1991, now abandoned which is a Continuation of application Ser. No. 07/208,102, filed Jun. 17, 1988, now abandoned.

The present invention relates to chromane derivatives having an antihypertensive and antiarrhythmic activity.

Belgian patent 829 611,(which corresponds to U.S. Pat. Nos. 4,048,317; 4,062,870; 4,107,317 and 4,110,347) mentions a whole series of chroman-3-ol derivatives having an antihypertensive activity; these derivatives are characterized by the presence of a group $NR_1R_2$ in the 4-position, in which $R_1$ is hydrogen or an optionally substituted hydrocarbon group and $R_2$ is hydrogen or an alkyl, it being possible for $NR_1R_2$ to be a heterocyclic group containing from 3 to 8 atoms, which is unsubstituted or substituted by one or two methyl groups, and by the presence, in some cases, of a large number of possible substituents in the 6-position or 7-position.

European patent application published under number 76 075(which corresponds to U.S. Pat. Nos. 4,446,113; 4,542,149; 4,640,928 and 4,644,070) describes chroman-3-ol derivatives having an antihypertensive activity which are characterized by the presence of a 2-oxopyrrolidin-1-yl group or a 2-oxopiperidin-1-yl group in the 4-position and by the presence, in some cases, of numerous possible substituents, including the cyano group, in the 6-position or 7-position.

It has now been found that 2,2-dimethylchroman-3-ol derivatives characterized by the presence, in the 4-position, of a nitrogen atom forming part of a 6-membered heterocycle containing 2 double bonds conjugated with an oxo group possess an excellent antihypertensive and antiarrhythmic activity and a very low toxicity.

Thus, according to one aspect, the present invention relates to trans-2,2-dimethylchroman-3-ol derivatives of the formula:

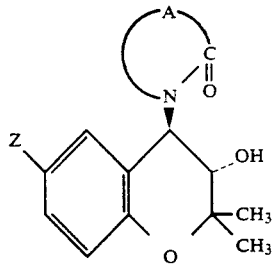

(I)

in which:

A, between N and CO, represents the group —CH═CH—E═CH— or the group

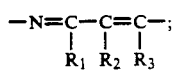

Z represents a halogen or a cyano, acetyl, trifluoroacetyl, nitro, alkylthio, carboxyl, phosphono, dialkoxyphosphoryl or alkoxycarbonyl group, the alkylthio and alkoxy groups containing from 1 to 3 carbon atoms;

E represents a nitrogen atom or a group $C(R_4)$;

$R_1$ represents hydrogen, a methyl group or a hydroxyl group and $R_2$ and $R_3$ each independently represent hydrogen or a methyl group, it being possible for only one of the substituents $R_1$, $R_2$ and $R_3$ to be methyl; and $R_4$ represents a hydrogen atom, a halogen atom, a methyl group or a hydroxyl group;

and to the pharmaceutically acceptable salts of the phosphono or carboxyl group.

In the present description and in the claims which follow, halogen is understood as meaning a fluorine, chlorine or bromine atom.

The pharmaceutically acceptable salts are preferably those of alkali metals and alkaline earth metals, such as the sodium and potassium salts, or those of organic bases such as triethanolamine, trometamol, ethanolamine, N-methylpiperidine or tert-butylamine.

The compounds (I) according to the invention have two asymmetric carbons in the 3-position and 4-position of the chromane ring. The present invention includes each of the stereoisomers of I as well as the racemate.

The present invention also relates to a process for the preparation of the compounds (I).

The said process comprises treating a chromane epoxide of the formula:

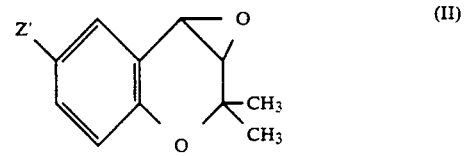

(II)

in which Z' has the same meaning as that given above to Z, but is not the carboxyl group or the phosphono group, with a heterocycle corresponding to one of the following tautomeric forms:

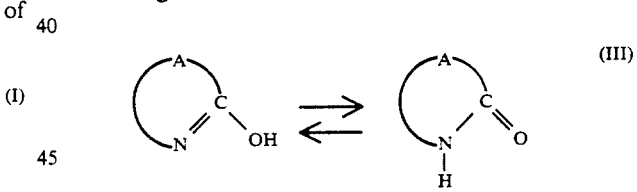

(III)

in which A, between N and CO or C(OH), has the meaning indicated previously for (I); if appropriate, converting the alkoxycarbonyl group to a carboxyl group or the dialkoxyphosphoryl group to a phosphono group; and, if appropriate, converting the resulting carboxylic acid or phosphonic acid to one of their pharmaceutically acceptable salts.

The reaction for opening the epoxide (II) is carried out at a temperature between 10° C. and 100° C. in an inert organic solvent such as dioxane, tetrahydrofuran, methyl tert-butyl ether, dimethyl sulfoxide or dimethylformamide, in the presence of a basic condensation agent such as sodium hydride or a quaternary ammonium hydroxide like benzyltrimethylammonium hydroxide. Under these operating conditions, the opening of the epoxide (II) leads to compounds of formula I having the trans configuration.

When the reaction is complete, a compound of the formula:

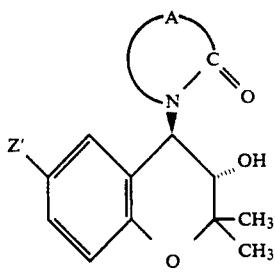

(Ia)

in which A and Z' are as defined above, is obtained which is isolated by the conventional methods.

When Z' represents an alkoxycarbonyl group, the conversion to a carboxyl group is effected by known methods.

When Z' represents a dialkoxyphosphoryl group, this can be converted to the corresponding phosphono group by transesterification with a trimethylsilyl halide, preferably the bromide, and hydrolysis of the di(trimethylsilyl ester) simply by reaction with water. This gives a compound of formula I in which Z represents a carboxyl or phosphono group and the said compound can be converted to one of its pharmaceutically acceptable salts, for example those of alkali metals or alkaline earth metals, such as the sodium or potassium salts, or those of organic bases such a& triethanolamine, trometamol, ethanolamine, tert-butylamine or N-methylpiperidine.

The starting epoxides of formula II are known or prepared by known methods. Thus the epoxide (II) in which Z' represents the cyano group is described in Belgian patent 852 955 (which corresponds to U.S. Pat. No. 4,251,537); the epoxides (II) in which Z' represents the nitro group, the acetyl group or an alkoxycarbonyl group are described in J. Med. Chem., 1983, 26, 1582–1589; the epoxides (II) in which Z' represents an alkylthio group are prepared by an analogous method; and the epoxides (II) in which Z' represents a halogen are prepared according to Tetrahedron, 1981, 37, (15), 2613–2616.

The compounds of formula II in which Z' represents a trifluoroacetyl group or a dialkoxyphosphoryl group are not described in the literature. These compounds are prepared from the corresponding chromene of the formula:

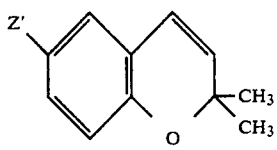

(IV)

with which N-bromosuccinimide is reacted, in aqueous dimethyl sulfoxide, to give the bromine derivative of the formula:

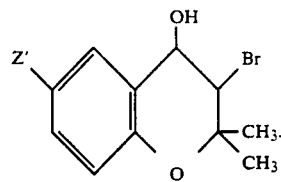

(V)

This compound (V) is treated with an alkaline agent in a water/organic solvent mixture, for example water/dioxane, preferably at room temperature, for a period of 8 to 20 hours, and the resulting epoxide of formula II is isolated by conventional methods, for example by concentration of the reaction mixture, recovery of the residue with a solvent which removes the impurities, such as methylene chloride, washing with water and concentration.

When Z' represents a dialkoxyphosphoryl group, the chromene IV can be prepared from 6-bromo-2,2-dimethylchromene (J. Chem. Soc., 1960, 3094–3098) of the formula:

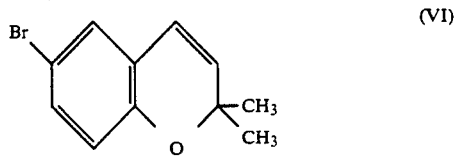

(VI)

by reaction with a trialkyl phosphite in the presence of nickel chloride at 180° C.

When Z' represents the trifluoroacetyl group, the chromene (IV) can be prepared from 4-trifluoroacetylphenol (J. Med. Chem., 1965, 8, 229) by the addition of 3-chloro-3-methylbut-1-yne in a basic medium, in the presence of a phase transfer catalyst.

The heterocycles of formula (III) are known and commercially available or are prepared by known methods.

The compounds according to the invention increase the polarization of smooth muscle fibers and have a vasodilative effect on the portal vein; their antihypertensive effect has been observed in animals.

Furthermore, it has been observed that the compounds according to the invention accelerate the repolarization of myocardial cells; their antiarrhythmic effect has been observed in parallel on an animal model.

No signs of toxicity are observed with these compounds at the pharmacologically active doses.

Thus the compounds obtained according to the invention can be used in the treatment of hypertension and pathological disorders associated with contractions of the smooth muscle fibers of the gastrointestinal, respiratory, uterine and urinary apparatuses, for example ulcers, asthma, premature uterine contraction and incontinence, and in the treatment of other cardiovascular pathological disorders such as angor, cardiac insufficiency and cerebral and peripheral vascular diseases. Furthermore, the compounds according to the invention can be used in the treatment of cardiac arrythmia.

Lastly, the compounds according to the invention can be used for the topic treatment of alopecia.

The present invention also relates to pharmaceutical compositions containing an effective dose of a compound according to the invention and suitable excipients. The said excipients are chosen according to the pharmaceutical form and the desired mode of administration.

In the pharmaceutical compositions of the present invention for oral, sublingual, subcutaneous, intramuscular, intravenous, topical, percutaneous or rectal administration, the active principles of formula I above, or their salts if appropriate, can be administered to animals and humans in unit forms of administration, mixed with conventional pharmaceutical carriers, for the prophylaxis or treatment of the above disorders or diseases. The appropriate unit forms of administration include oral forms such as tablets, gelatin capsules, powders, granules and solutions or suspensions to be taken orally, sublingual and buccal forms, subcutaneous, intramuscular and intravenous forms and rectal forms.

For topical administration, the compounds according to the invention can be used in creams, ointments, pomades or lotions.

To achieve the desired prophylactic or therapeutic effect, the daily dose of active principle can vary between 0.01 and 5 mg per kg of body weight.

Each unit dose can contain from 0.5 to 200 mg, preferably from 1 to 50 mg, of active ingredients combined with a pharmaceutical carrier. This unit dose can be administered 1 to 5 times a day so as to administer a daily dosage of 0.5 to 1000 mg, preferably 1 to 250 mg.

When a solid composition is prepared in the form of tablets, the main active ingredient is mixed with a pharmaceutical vehicle such as gelatin, starch, lactose, magnesium stearate, talc, gum arabic or the like. The tablets can be coated with sucrose, a cellulose derivative or other appropriate substances or they can be treated so as to have a sustained or delayed activity and so as to release a predetermined amount of active principle continuously.

A preparation in the form of gelatin capsules is obtained by mixing the active ingredient with a diluent and pouring the mixture obtained into soft or hard gelatin capsules.

A preparation in the form of a syrup or elixir or for administration in the form of drops can contain the active ingredient together with a sweetener, which is preferably calorie-free, methylparaben and propylparaben as antiseptics, an agent for imparting taste and an appropriate colorant.

Water-dispersible powders or granules can contain the active ingredient mixed with dispersants or wetting agents, or suspending agents such as polyvinylpyrrolidone, as well as with sweeteners or taste correctors.

For rectal administration, suppositories are used which are prepared with binders melting at rectal temperature, for example cacao butter or polyethylene glycols.

For parenteral administration, aqueous suspensions, isotonic saline solutions or injectable sterile solutions are used which contain pharmacologically compatible dispersants and/or wetting agents, for example propylene glycol or butylene glycol.

The active principle can also be formulated as microcapsules, if appropriate with one or more carriers or additives.

The compositions of the present invention can contain, in addition to the products of formula I above or one of their pharmaceutically acceptable salts, other active principles such as, for example, tranquilizers or other drugs which can be useful in the treatment of the disorders or diseases indicated above.

The following Examples illustrate the invention without however implying a limitation. In the Examples, as well as in the descriptive part and in the claims, the products are denoted as chromane derivatives. It is understood that the products of the present invention are 2,2-dimethyl-3,4-dihydro-2H-chromene derivatives and that the term "chromane" denotes "3,4-dihydro-2H-chromene".

PREPARATION I a) 6-Diethylphosphono-2,2-dimethyl-2H-chromene 16 g of 6-bromo-2,2-dimethyl-2H-chromene are dissolved in 100 ml of triethyl phosphite. 2 g of nickel chloride are added and the mixture is heated at 180° C. for 24 hours in an autoclave. After the remaining triethyl phosphite has been concentrated, the expected product distils at 130°-140° C. under 133.322 Pa. 11.5 g are collected.

b) trans-3-Bromo-6-diethylphosphono-2,2-dimethylchroman-4-ol 11 g of the previous product are dissolved in 62 ml of dimethyl sulfoxide containing 1.35 ml of water. 12.2 g of N-bromosuccinimide are added in small portions while the solution is kept at a temperature below 20° C. The mixture is stirred at room temperature for 30 minutes, 100 ml of water are then added and extraction is carried out with ethyl acetate. After drying over sodium sulfate, the organic phase is concentrated, the residue is taken up with 100 ml of acetone and 50 ml of water and the mixture is then refluxed for 5 hours. The acetone is concentrated, the residue is extracted with ether and the extract is dried over sodium sulfate and concentrated. The expected product crystallizes from isopropyl ether. After the crystals have been filtered off and dried, 3.2 g of product are collected.

Melting point: 124° C.

c) 6-Diethylphosphono-2,2-dimethyl-3,4-epoxychromane 23 g of the compound obtained in the previous step are mixed with 12 g of sodium hydroxide in 900 ml of dioxane and 100 ml of water. After 24 hours at room temperature, the dioxane is concentrated, the residue is taken up with water and extracted with ethyl ether and the extract is then dried over sodium sulfate. After concentration, 16.2 g of the expected product are obtained.

PREPARATION II a) 2,2-Dimethyl-6-trifluoroacetylchromene

A mixture containing the following is refluxed for 48 hours, with stirring: 8.4 g of 4-trifluoroacetylphenol (prepared according to J. Med. Chem., 1965, 8, 229), 1.8 g of sodium hydroxide pellets, 50 ml of methylene chloride, 30 ml of water, 11 g of a 35% methanolic solution of benzyltrimethylammonium hydroxide, 14 ml of tris(3,6-dioxaheptyl)amine and 6.1 g of 3-chloro-3-methylbut-1-yne. 11 g of 3-chloro-3-methylbutyne are added and the mixture is kept under reflux for 4 days. 50 ml of water and 100 ml of methylene chloride are then added, the mixture is left to separate and the organic phase is washed with 1N sodium hydroxide solution and then with water, dried and then concentrated under vacuum to give 10 g of an oil, which is used in the crude state for cyclization. 40 ml of 1,2-dichlorobenzene are added and the mixture is refluxed for 2 hours. It is concentrated under vacuum and the residue is then taken up in 40 ml of hexane and chromatographed on a column of 300 g of silica using isopropyl ether as the eluent. This gives 3.5 g of a yellow oil.
Yield: 40%.
TLC on silica (hexane/acetone: 7/3): Rf=0.66.
The IR and NMR spectra confirm the structure.

b)
3-Bromo-2,2-dimethyl-4-hydroxy-6-trifluoroacetylchromane 3.4 g of 2,2-dimethyl-6-trifluoroacetylchromene, prepared in the previous step, are mixed with 30 ml of dimethyl sulfoxide and 5 ml of water at 15° C., with stirring. 5 g of N-bromosuccinimide are added over a period of 20 minutes and the mixture is stirred for 2 hours. It is poured into iced water and the precipitate formed is filtered off, washed with water and then dried. After this has been dissolved in 300 ml of hexane, the insoluble material is filtered off and the filtrate is concentrated to give 3 g of a yellowish solid.
Yield: 68%.
Melting point: 103° C.
TLC on silica (hexane/acetone 7/3): Rf=0.55.
The IR and NF-IR spectra confirm the structure.

c) 2,2-Dimethyl-3,4-epoxy-6-trifluoroacetylchromane

A mixture containing 2.9 g of 3-bromo-2,2-dimethyl-4-hydroxy-6-trifluoroacetylchromane, prepared in the previous step, 25 ml of dioxane, 0.5 g of sodium hydroxide pellets and 5 ml of water is stirred at 20° C. for 20 hours. After concentration under vacuum at 40° C., the residue is treated 4 times with 100 ml of ethyl ether and the extracts are then dried and concentrated under vacuum to give 2 g of a yellow oil.
Yield: 90%.
TLC on silica (methylene chloride): Rf=0.80.
The IR and NMR spectra confirm the structure.

PREPARATION III

4-Fluoropyrid-2-one is prepared according to C. C. Leznoff et al., J. Het. Chem., 1985, 22, p. 145, in the following manner:

a) 2-Methoxypyridine N-oxide hydrochloride

This compound is obtained from 21.8 g of 2-methoxypyridine and 144.4 g of 45% aqueous metachloroperbenzoic acid in 500 ml of methylene chloride.
Weight: 23.6 g.
Yield: 61%.
Melting point: 123° C.

b) 2-Methoxy-4-nitropyridine N-oxide 30 ml of concentrated sulfuric acid, cooled to 0° C., are added to 15.5 g of 2-methoxypyridine N-oxide hydrochloride, after which 42 ml of fuming nitric acid and 14 ml of concentrated sulfuric acid are added dropwise at 0° C. After the temperature has been allowed to rise, the reaction mixture is heated for 3 hours at 90°–100° C. and is then cooled and poured onto 50 g of ice. It is neutralized to pH 7 by the addition of concentrated aqueous ammonia at a temperature below 10° C. The aqueous phase is extracted 6 times with methylene chloride, the organic phase is then dried over sodium sulfate and concentrated and 11 g of a yellow solid corresponding to a mixture of 2-methoxy-4-nitropyridine N-oxide and 2-methoxy-5-nitropyridine N-oxide are recovered.

The 2 products are separated by chromatography on silica using a methylene chloride/methanol mixture (95/5) as the eluent. 6.3 g of 2-methoxy-4-nitropyridine N-oxide are collected.
Melting point: 180° C.
Yield: 46.3%.

c) 4-Amino-2-methoxypyridine

A mixture of 6.3 g of 2-methoxy-4-nitropyridine N-oxide and 12.6 g of iron powder in 150 ml of acetic acid is heated for 1 hour at 100° C. After cooling, sodium hydroxide is added, the mixture is then filtered and the material on the filter is washed with water. The aqueous phase is extracted with ethyl ether. After drying and concentration, 3.6 g of an oil are recovered which crystallizes to a white solid.
Yield: 78.4%.
Melting point: 88° C.

d) 4-Fluoro-2-methoxypyridine

A solution containing 3.6 g of 4-amino-2-methoxypyridine in 15 ml of 48% fluoroboric acid is cooled to 10° C. 3 g of sodium nitrite are added in small portions at a temperature below −5° C. and the mixture is then stirred for 45 minutes at 0° C. It is brought slowly to room temperature and then stirred in a water bath for 30 minutes. It is cooled to −10° C. and then neutralized by the addition of 3M sodium hydroxide solution while being kept at low temperature. The mixture is extracted with 50 ml of ethyl ether and the organic phase is washed with 5 ml of cold water and dried over anhydrous potassium fluoride. The ether is distilled at atmospheric pressure. The oily residue is used as such in the next step.

e) 4-Fluoropyrid-2-one 5.85 g of iodotrimethylsilane in 3 ml of methylene chloride are added dropwise, under argon, to a solution of 3.3 g of the previously obtained product in 13 ml of methylene chloride. The mixture is stirred at room temperature for 4 hours and then heated at 40° C. for 1 hour and left overnight at room temperature. The solvent is concentrated under vacuum, 10 ml of methylene chloride are added and the mixture is concentrated again under vacuum. The residue obtained is dissolved in methylene chloride, a few crystals of sodium thiosulfate are added and the mixture is stirred until the brown coloration has disappeared. The mixture is filtered and the filtrate is dried over sodium sulfate. The inorganic residue is taken up in methanol and then filtered off. The inorganic residue is chromatographed on silica using a methylene chloride/methanol mixture (9/1) as the eluent. 0.590 g of a white solid is recovered.
Melting point: 172° C.

EXAMPLE 1 trans-6-Cyano-4-(1,2-dihydro-2-oxopyrid-1-yl)2,2-dimethylchroman-3-ol: SR 44 709

1 g of 6-cyano-2,2-dimethyl-3,4-epoxychromane is refluxed for 40 hours with 1 g of 2-hydroxypyridine in 10 ml of dioxane, in the presence of 0.20 ml of a methanolic solution containing 35% of benzyltrimethylammonium hydroxide. The mixture is taken up with 30 ml of water and the precipitate obtained is filtered off, washed with isopropyl ether and then recrystallized from 20 ml of absolute ethyl alcohol to give 0.9 g of the expected product.

Melting point: 243° C. with decomposition (capillary tube).

EXAMPLE 2 trans-6-Diethylphosphono-4-(192-dihydro-2-oxopyrid-1-yl)-2,2-dimethylchroman-3-ol: SR 44 745

A mixture containing 5.6 g of 6-diethylphosphono-2,2-dimethyl-3,4-epoxychromane (PREPARATION I), 2.5 g of 2-hydroxypyridine and 4 drops of benzyltrimethylammonium hydroxide is refluxed for 48 hours. After the dioxane has been concentrated, the residue is taken up in methylene chloride and the mixture is washed twice with water and then dried over sodium sulfate and concentrated to dryness. Ethyl ether is added and the product crystallizes. After recrystallization from ethyl acetate, 1.5 g of the expected product are obtained.

Melting point: 130.5° C. (capillary tube).

EXAMPLE 3 trans-4-(1,2-Dihydro-2-oxopyrid-1-yl)-2,2-dimethyl-6-trifluoroacetylchroman-3-ol: SR 45 160

A mixture containing 1.9 g of 2,2-dimethyl-3,4-epoxy-6-trifluoroacetylchromane (PREPARATION II), 1.4 g of 2-hydroxypyridine, 5 ml of dioxane and 0.2 ml of a methanolic solution containing 35% of benzyltrimethylammonium hydroxide is refluxed for 20 hours. The residue obtained after concentration under vacuum is taken up with 20 ml of water and the insoluble material is then filtered off and washed with water and boiling isopropyl ether. It is chromatographed on a column of 50 g of silica using a methylene chloride/ethyl acetate mixture (7/3) as the eluent. This gives 0.3 g of dry product.

Yield: 12%.

IR spectrum: 1150 cm$^{-1}$: C—O—C (chromane)
1665 cm$^{-1}$: CO (pyridone)
1720 cm$^{-1}$: CO (CF$_3$CO)
3670 cm$^{-1}$: OH

EXAMPLE 4 trans-6-Cyano-4-(I,2-dihydro-4-hydroxy-2-oxopyrid-1-yl)-2,2-dimethylchroman-3-ol: SR 44 793

3 g of 6-cyano-2,2-dimethyl-3,4-epoxychromane are refluxed for 20 hours with 1.8 g of 2,4-dihydroxypyridine in 30 ml of dioxane and 20 ml of dimethylformamide, in the presence of 0.6 ml of a methanolic solution containing 35% of benzyltrimethylammonium hydroxide. The solvents are evaporated off under vacuum and the residue is then crystallized by the addition of isopropyl ether. The crystals obtained are taken up with water, filtered off and then washed with acetone to give 850 mg of the expected product.

Melting point: 248°-250° C.

EXAMPLE 5 trans-6-Cyano-4-(1,6-dihydro-6-oxopyridazin-1-yl)-2,2-dimethylchroman-3-ol: SR 44 758

1 g of 6-cyano-2,2-dimethyl-3,4-epoxychromane and 1 g of 3-hydroxypyridazine are refluxed for 20 hours in 5 ml of dioxane, in the presence of 0.20 ml of a methanolic solution containing 35% of benzyltrimethylammonium hydroxide. The mixture is concentrated under vacuum and the residue is then triturated in 20 ml of water; the precipitate obtained is filtered off, washed with water and isopropyl ether and then recrystallized from 10 ml of isopropyl alcohol to give 0.9 g of the expected product.

Melting point: 211°-215° C.—Rf/silica (ethyl acetate): 0.34.

EXAMPLE 6 trans-6-Cyano-4-(I,6-dihydro-3-hydroxy-6-oxopyridazin-1-yl)-2,2-dimethylchroman-3-ol: SR 44 994

A mixture containing I g of 6-cyano-2,2-dimethyl-3,4-epoxychromane, 1.1 g of 3,6-dihydroxypyridazine and 0.20 ml of a methanolic solution containing 357. of benzyltrimethylammonium hydroxide, in 5 ml of dioxane and 5 ml of dimethylformamide, is refluxed for 50 hours. It is concentrated under vacuum and the residue is then triturated in 15 ml of water. The precipitate formed is filtered off and washed with water and then isopropyl ether.

It is crystallized from 60 ml of 95% ethanol to give 0.7 g of the expected product.

Melting point: 251°-252° C.—Rf/silica (ethyl acetate/ethanol: 8/2): 0.63.

EXAMPLES 7 and 8 trans-6-Cyano-4-(I,6-dihydro-3-hydroxy-5-methyl-6-oxopyridazin-1-yl)-2,2-dimethylchroman-3-ol: SR 45 209 (Ex. 7)

trans-6-Cyano-4-(I,6-dihydro-3-hydroxy-4-methyl-6-oxopyridazin-1-yl)-2,2-dimethylchroman-3-ol: SR 45 218 (Ex. 8)

A mixture containing 2 g of 6-cyano-2,2-dimethyl-3,4-epoxychromane, 2.5 g of 3,6-dihydroxy-4-methyl-pyridazine, 30 ml of dimethylformamide and 0.4 ml of a methanolic solution containing 35% of benzyltrimethylammonium hydroxide is kept at 120° C. for 8 hours.

It is concentrated under vacuum and the residue is then triturated in 30 ml of water, filtered off, washed with absolute ethanol and then crystallized from 40 ml of methanol to give 1.3 g of a mixture of 2 products, which are separated by chromatography on a silica column.

SR 45 209: Rf (ethyl acetate/ethyl alcohol: 8/2): 0.80

SR 45 218: Rf (ethyl acetate/ethyl alcohol: 8/2): 0.71

The structures of the 2 products are confirmed by analysis of their NMR spectra run at 250 MHz in DMSO.

The following abbreviations are used to describe the spectra:

s=singlet
d=doublet
m=multiplet or unresolved signals
J=coupling constant

---

NMR SPECTRUM

-continued

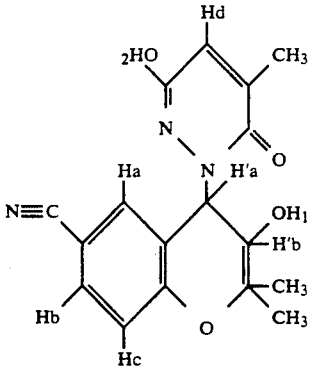

| Delta ppm | Appearance | Protons | Assignment |
|---|---|---|---|
| 1.25 | 2s | 6H | 2CH$_3$ |
| 1.40 | | | |
| 2.09 | s | 3H | CH$_3$ (pyridazine) |
| 3.80 | d of d J=6Hz, J=8Hz | 1H | H'b |
| 5.87 | d, J=8Hz | 1H | H'a |
| 5.90 | d, J=6Hz | 1H | OH$_1$ |
| 6.95 | d, J=10Hz | 1H | Hc |
| 7.19 | s | 1H | Hd |
| 7.67 | d of d J=10Hz, J=2Hz | 1H | Hb |
| 7.73 | d, J=2Hz | 1H | Ha |
| 12 | s | 1H | OH$_2$ |

NMR SPECTRUM

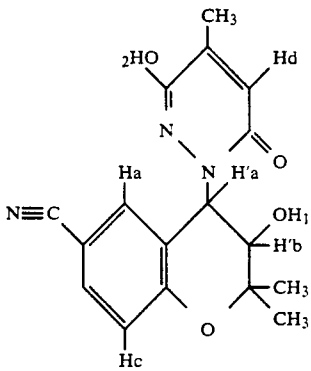

| Delta ppm | Appearance | Protons | Assignment |
|---|---|---|---|
| 1.29 | 2s | 6H | 2CH$_3$ |
| 1.40 | | | |
| 2.09 | s | 3H | CH$_3$ (pyridazine) |
| 3.83 | d of d J=4Hz, J=6Hz | 1H | H'b |
| 5.78 | d, J=6Hz | 1H | H'a |
| 5.90 | d, J=4Hz | 1H | OH$_1$ |
| 6.80 | s | 1H | Hd |
| 7.00 | d, J=8Hz | 1H | Hc |
| 7.68 | d, J=8Hz | 1H | Hb |
| 7.78 | s | 1H | Ha |
| 12.10< >11.8 | s broad | 1H | OH$_2$ |

EXAMPLE 9 trans-6-Cyano-4-(I,6-dihydro-3-methyl-6-oxopyridazin-1-yl)-2,2-dimethylchroman-3-ol: SR 45 225

A mixture is prepared which contains 1 g of 6-cyano-2,2-dimethyl-3,4-epoxychromane and 1.1 g of 6-methyl-pyridazin-3-one (prepared by the method described in J. Chem. Soc., 1947, p. 241, by reacting ethyl levulinate with hydrazine hydrate) in 10 ml of dioxane containing 0.1 ml of a 35% methanolic solution of benzyltrimethylammonium hydroxide. After 2 days at room temperature, the mixture is diluted with water and filtered, the material on the filter is dissolved in ethyl acetate, the water is then decanted and the organic phase is dried and concentrated. After recrystallization from an ethyl acetate/isopropyl ether mixture, 0.6 g of the expected product is obtained.

Melting point: >257° C.

The product is characterized by its NMR spectrum run at 250 MHz.

NMR SPECTRUM

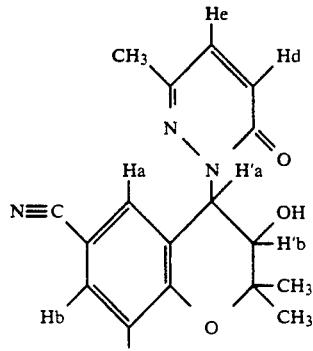

| Delta ppm | Appearacne | Protons | Assignment |
|---|---|---|---|
| 1.25 | s | 6H | 2CH$_3$ |
| 1.46 | s | | |
| 2.2 | s | 3H | CH$_3$ (pyridazine) |
| 4.15 | m | 1H | H'b |
| 5.78 | d, J=8Hz | 1H | OH |
| 6 | m | 1H | H'a |
| 6.96 to 7.68 | m | 5H | Ha, Hb, Hc, Hd, He |

EXAMPLE 10 trans-6-Cyano-4-(1,2-dihydro-4-fluoro-2-oxopyrid-1-yl)-2,2-dimethylchroman-3-ol: SR 45 311

A mixture containing 460 mg of 6-cyano-2,2-dimethyl-3,4-epoxychromane, 283 mg of 4-fluoropyrid-2-one (PREPARATION III) and 0.05 ml of a methanolic solution containing 35% of benzyltrimethylammonium hydroxide, in 5 ml of tetrahydrofuran, is refluxed for 24 hours. The solvent is concentrated, the residue is taken up in ethyl acetate and the organic phase is then washed with water, dried over sodium sulfate and concentrated under vacuum. The residue obtained is chromatographed on silica using a methylene chloride/methanol mixture (97/3) as the eluent. 200 ml of a white solid are recovered.

Melting point: 235° C.

The compounds according to the invention which are collated in Table 1 below were also prepared by following similar procedures.

TABLE 1
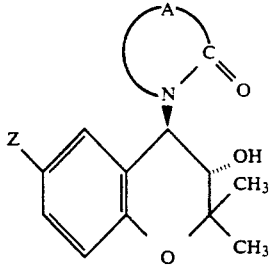
| Example no. | Product no. | Z | ⟨A⟩N-C=O | Melting point (solvent of recrystallization) |
|---|---|---|---|---|
| 11 | SR 45 012 | CN | 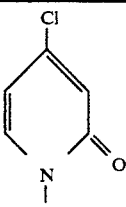 | 260–261° C. (AcOEt) |
| 12 | SR 45 067 | CN | 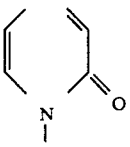 | 251–253° C. (AcOEt/CH$_2$Cl$_2$) |
| 13 | SR 45 135 | CN | 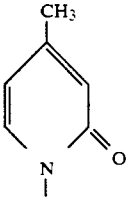 | 266–267° C. (THF) |
| 14 | SR 45 373 | Br | 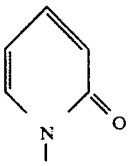 | 248° C. ((iPr)$_2$O) |
| 15 | SR 45 434 | Cl | 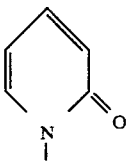 | 250° C. (AcOEt) |
| 16 | SR 45 484 | CH$_3$CO | 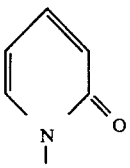 | 260° C. (THF) |

TABLE 1-continued

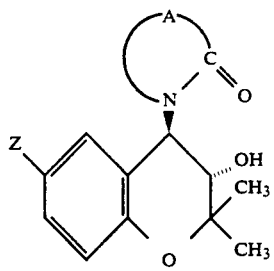

| Example no. | Product no. | Z | 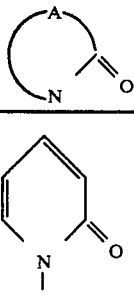 | Melting point (solvent of recrystallization) |
|---|---|---|---|---|
| 17 | SR 45 485 | NO$_2$ | | 224–226° C. (AcOEt) |
| 18 | SR 45 512 | CH$_3$S | | 154° C. |

Where the product was recrystallized, the solvent of recrystallization is indicated in brackets. The abbreviations used have the following meanings:
AcOEt: ethyl acetate
THF: tetrahydrofuran
(iPr)$_2$O: isopropyl ether Pharmaceutical compositions containing the product according to the invention were prepared.

EXAMPLE 19

Coated Tablet

Tablets can be prepared by wet granulation. Ethyl alcohol and purified water are used as auxiliary production solvents. After evaporation of these solvents, magnesium stearate is introduced in an external phase as a lubricant. The tablets are then coated.

| Formulation | |
|---|---|
| SR 44 709 | 1 mg |
| 95% ethyl alcohol | 0.02 ml |
| Microcrystalline cellulose | 48 mg |
| Lactose | 69.8 mg |
| Magnesium stearate | 1.2 mg |
| Purified water | qs for 120 mg |
| Coating formula: | |
| Methyl hydroxypropyl cellulose, 6 cps | 0.14 mg |
| Titanium dioxide | 0.04 mg |
| Polyoxyethylene glycol 6000 | 0.02 mg |
| Purified water | 1.8 mg |
| Talc for film-coated tablets | qs for 122 mg coated tablet |

EXAMPLE 20

| Injectable form | |
|---|---|
| SR 44 709 | 1 mg |
| Polyoxyethylene glycol 400 | 0.5 ml |
| Purified water for injectable preparations | qs for 1 ml |

EXAMPLE 21

| Injectable form | |
|---|---|
| SR 44 709 | 1 mg |
| Polysorbate 80$^R$ | 0.1 ml |
| Propylene glycol | 0.1 g |
| Purified water for injectable preparations | qs for 1 ml |

The products according to the invention were studied in the in vitro and in vivo pharmacology tests A), B) and C) below.

trans-6-Cyano-4-(2-oxopyrrolidin-1-yl)-2,2-dimethyl-chroman-3-ol:

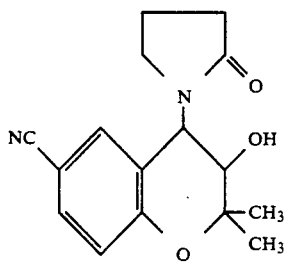

described in European patent 76075 and hereafter referred to as "Product A", was used as the reference compound and tested under the same conditions.

A) Isolated Rat Portal Vein

Male Sprague Dawley rats (250-300 g) are stunned and then bled after their throats have been cut. The portal vein, ligated in situ at two points 15 mm apart, is isolated, cut longitudinally and then mounted vertically in an experimental cell containing a physiological solution, at 37° C., of the following composition (mmol/l): NaCl:137; KCl: 5.4; MgCl$_2$: 1.05; CaCl$_2$: 1.8; NaH$_2$PO$_4$: 1.2; NAHCO$_3$: 15.5; glucose: 11.5, into which a mixture of gases containing 95% of oxygen and 5% of carbon dioxide is bubbled.

The vein is subjected to a tension of 500 mg. After a period of stabilization (about 1 h 30 min), the spontaneous contractile activities are recorded with the aid of an isometric sensor. Each measurement is performed successively on 4 preparations.

The product is studied at successive increasing concentrations (15 min per concentration) until the spontaneous contractions have been totally inhibited. The results are expressed in the form of the molar concentration which causes a 50 per cent inhibition of the spontaneous contractile activities (IC$_{50}$).

The results obtained are collated in Table 2 below.

The results column shows the IC$_{50}$ of the spontaneous contractile activities of isolated rat portal vein.

TABLE 2

| Inhibition of spontaneous contractile activities | | |
|---|---|---|
| Product | Example | IC$_{50}$M |
| SR 44 709 | 1 | $9.0 \cdot 10^{-8}$ |
| SR 44 758 | 5 | $1.3 \cdot 10^{-7}$ |
| SR 44 793 | 4 | $3.4 \cdot 10^{-8}$ |
| SR 44 994 | 6 | $9.0 \cdot 10^{-9}$ |
| SR 45 012 | 11 | $2.6 \cdot 10^{-8}$ |
| SR 45 067 | 12 | $7.7 \cdot 10^{-8}$ |
| SR 45 135 | 13 | $8.0 \cdot 10^{-8}$ |
| SR 45 209 | 7 | $5.8 \cdot 10^{-8}$ |
| SR 45 218 | 8 | $2.0 \cdot 10^{-8}$ |
| SR 45 225 | 9 | $8.8 \cdot 10^{-8}$ |
| SR 45 311 | 10 | $5.0 \cdot 10^{-8}$ |
| Product A | — | $6.8 \cdot 10^{-8}$ |

All the compounds studied have a substantial inhibitory activity against the spontaneous contractions of the vein, which is at least of the same order as that of the reference product. Four of the compounds—SR 44 994, SR 44 793, SR 45 012 and SR 45 218—whose IC$_{50}$ values are equal to or less than $3.4 \cdot 10^{-8}$, are at least 5 times more active than Product A in this test.

B) Guinea-pig Papillary Muscle

Male Albino Charles River guinea-pigs (300–400 g) are stunned and then bled after their throats have been cut. The heart is isolated and opened and the right papillary muscle is excised and then kept alive in an experimental cell containing a physiological solution at 36° C. (composition described above).

The preparation is stimulated with the aid of a bipolar electrode connected to a stimulator (frequency=60 beats per minute). The ventricular action potential is measured by the conventional microelectrode method. The characteristic parameters were measured on the action potentials (AP) before and after the introduction of the test product at 3 successive increasing concentrations (30 minutes of perfusion per concentration). The concentration which produces a 50 per cent reduction in the duration of the AP is indicated (IC$_{50}$).

The results are reported in Table 3 below:

TABLE 3

| | Duration of the action potential | |
|---|---|---|
| Product | Example | IC$_{50}$ |
| SR 44 709 | 1 | $2.0 \cdot 10^{-5}$ |
| SR 44 793 | 4 | $2.7 \cdot 10^{-6}$ |
| SR 44 994 | 6 | $4.0 \cdot 10^{-6}$ |
| Product A | — | $1.6 \cdot 10^{-5}$ |

The Table shows that the duration of the action potential is markedly decreased. In particular, the concentrations of SR 44 793 and SR 44 994 which produce a 50 per cent reduction in this parameter are 5 to 10 times lower than that of Product A, demonstrating a greater electrophysiological activity on the membrane permeability responsible for this repolarization phase.

The electrophysiological profiles of the 3 compounds studied are similar: no significant effect on the rest potential and the maximum depolarization rate; this means that the compounds studied have no local anesthetic activity.

C) Antihypertensive Activity on Vigilant Spontaneously Hypertensive Rats (SHR)

The experiment is performed on male SHR (of the Wistar strain) aged between 11 and 12 weeks; under pentobarbital anesthesia, a catheter is implanted in a carotid artery on the day before the experiment. In the experiment, the diastolic pressure (DP) and systolic pressure (SP) of the vigilant animals are recorded continuously 1 hour before and up to 2 hours after administration of the product. The heart rate (HR) is determined from the pulse pressure and recorded continuously for the same time.

The products were administered orally in a volume of 2 ml per 100 g of body weight after suspension in a 5% aqueous solution of gum arabic.

The results are reported in Table 4 below.

TABLE 4

| | Decrease in blood pressure | | |
|---|---|---|---|
| Product | Example | Dose mg/kg p.o. | Maximum decrease in mean blood pressure mm of mercury ($\pm$s.e.) |
| SR 44 709 | 1 | 0.06 | 21 $\pm$ 5 |
| | | 0.10 | 39 $\pm$ 12 |
| SR 44 758 | 5 | 0.03 | 12 $\pm$ 2 |
| | | 0.10 | 33 $\pm$ 5 |
| SR 44 793 | 4 | 0.03 | 22 $\pm$ 2 |
| | | 0.06 | 26 $\pm$ 3 |
| | | 0.10 | 50 $\pm$ 9 |
| SR 44 994 | 6 | 0.03 | 14 $\pm$ 0 |
| | | 0.10 | 37 $\pm$ 4 |
| Product A | — | 0.03 | 16 $\pm$ 5 |
| | | 0.10 | 30 $\pm$ 10 | s.e. = standard error

The products according to the invention are powerful antihypertensives with an activity of the same order as that of Product A.

On the other hand, it was found that two of the compounds representative of the present invention—SR 44 793 and SR 44 994—have a longer duration of action than Product A.

The products of the invention were also studied as antiarrhythmics in test D) below.

D) Antiarrhythmic Activity on Vigilant Dogs

The method used is that described by Dupuis et al. (Br. J. Pharmacol., 1976, 58, p. 409), in which an acute infarction is caused by the insertion of a copper spiral into the coronary circulation, with the thorax closed off. The electrocardiogram is measured by telemetry and the extrasystoles are analyzed and counted automatically while the animal is being monitored by an internal television circuit. The products were administered orally to animals presenting at least 50 percent of extrasystoles.

Two compounds representative of the present invention—SR 44 709 administered orally at a dose of 1 mg/kg and SR 44 793 administered orally at a dose between 0.1 and 0.5 mg/kg—showed a substantial antiarrhythmic activity by reducing the number of extrasystoles or by restoring a sinus rhythm for a period varying from 2 hours to 10 hours according to the animals.

The biological data above show that the compounds according to the invention are powerful antihypertensives and potential antiarrhythmics.

The acute toxicity of one product representative of the invention—SR 44 709—was measured on a group of 10 mice by oral administration at doses of 10, 50, 500 and 1000 mg/kg and compared with that of Product A. In the case of SR 44 709, all the animals survived at a dose of 1000 mg/kg, whereas in the case of Product A, all 10 animals died at a dose of 1000 mg/kg.

What is claimed is:

1. A method for the treatment of asthma comprising administering an effective amount to treat asthma of a compound of formula:

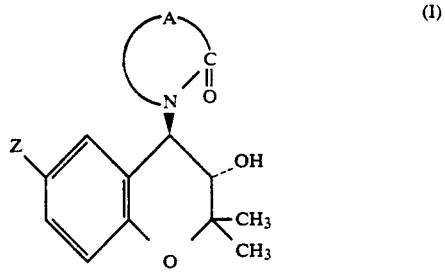

in which:
- A, between N and CO, represents the group —CH=CH—E=CH— $R_1 R_2 R_3$
- Z represents a cyano, trifluoroacetyl, phosphono, dialkoxyphosphoryl or the alkoxy groups having from 1 to 3 carbon atoms;
- E represents a group $C(R_4)$;
- $R_4$ represents a hydrogen atom or a hydroxyl group except that Z is trifluoroacetyl only when $R_4$ is hydrogen;

and the pharmaceutically acceptable salts of the phosphono, together with a pharmaceutically acceptable excipient.

2. A method of treatment of a patient suffering from asthma which comprises administering to the patient a pharmaceutical composition comprising an effective amount of (trans)-6-cyano-4-(1,2-dihydro-2-oxopyrid-1-yl)-2,2-dimethylchroman-3-ol and a pharmaceutically acceptable excipient.

* * * * *